United States Patent
Twomey et al.

(10) Patent No.: US 8,968,285 B2
(45) Date of Patent: Mar. 3, 2015

(54) PORTABLE SURGICAL INSTRUMENTS

(75) Inventors: John R. Twomey, Longmont, CO (US); William E. Robinson, Boulder, CO (US); Jason L. Craig, Loveland, CO (US)

(73) Assignee: Covidien LP, Mansfield, MA (US)

(*) Notice: Subject to any disclaimer, the term of this patent is extended or adjusted under 35 U.S.C. 154(b) by 687 days.

(21) Appl. No.: 13/312,299

(22) Filed: Dec. 6, 2011

(65) Prior Publication Data

US 2013/0144285 A1    Jun. 6, 2013

(51) Int. Cl.
*A61B 18/10*    (2006.01)

(52) U.S. Cl.
USPC .............................. 606/30; 606/52

(58) Field of Classification Search
USPC .................. 606/41, 42, 45, 47, 30, 34, 51, 52
See application file for complete search history.

(56) References Cited

U.S. PATENT DOCUMENTS

| | | | |
|---|---|---|---|
| 5,207,697 A | 5/1993 | Carusillo et al. | |
| 5,747,953 A | 5/1998 | Philipp | |
| D439,334 S | 3/2001 | Hershberger et al. | |
| 7,909,221 B2 | 3/2011 | Viola et al. | |
| 8,435,257 B2 * | 5/2013 | Smith et al. | 606/169 |
| 2011/0257650 A1 | 10/2011 | Deville et al. | |

* cited by examiner

*Primary Examiner* — George Evanisko

(57) ABSTRACT

A portable surgical instrument (PSI) includes a shaft extending therefrom. An end effector operably supported at the distal end of the shaft includes a pair of jaw members. One or both of the jaw members is activatable to treat tissue. A selectively removable generator pivotally couples to the housing to energize the activatable jaw member. The generator defining one or more apertures at a distal end thereof and a pivot member disposed at a proximal end thereof. A locking mechanism configured to operably couple to the elongated shaft of the housing includes one or more locking fingers configured to releasably couple to the one or more apertures disposed at the distal end of the generator such that generator is selectively and removably engageable with the housing of the portable surgical instrument.

16 Claims, 8 Drawing Sheets

PORTABLE SURGICAL INSTRUMENTS

BACKGROUND

1. Technical Field

The present disclosure relates to portable surgical instruments and, more particularly, to portable surgical instruments including a generator configured to selectively and removably couple thereto via a "quick-release" locking mechanism of the portable surgical instrument.

2. Background of Related Art

Portable surgical instruments are known in the medical arts. Portable surgical instruments overcome some of the drawbacks that are typically associated with surgical instruments that draw power from electrical outlets. That is, outlet driven surgical instruments utilize power cords that may create tripping and/or entanglement hazards in an operating room environment.

Typically, the portable surgical instrument includes a battery or battery assembly that is configured to removably couple or "latch" to the portable surgical instrument. In addition, the portable surgical instrument may be configured to include one or more selectively removable generators that communicate with the battery assembly to provide energy to an end-effector assembly that is associated with the portable surgical instrument. One or more suitable locking mechanisms may be associated with the portable surgical instrument to secure the generator to the portable surgical instrument. For example, in one particular instance, a locking knob may be operably coupled to a proximal end of the portable surgical instrument and configured to screw into the generator to secure the generator to the portable surgical instrument. In this instance, the locking knob may be, initially, hand tightened and, subsequently, further tighten via a wrench or other suitable device to properly secure the generator to the portable surgical instrument.

As can be appreciated, generators that are configured to quickly and easily couple or latch to the portable surgical instrument may prove advantageous in the surgical environment.

SUMMARY

As can be appreciated, generators that are configured to quickly and easily couple or latch to the portable surgical instrument may prove advantageous in the surgical environment.

In the drawings and in the descriptions that follow, the term "proximal," as is traditional, will refer to an end that is closer to the user, while the term "distal" will refer to an end that is farther from the user.

An aspect of the disclosure provides a portable surgical instrument. The portable surgical instrument includes a housing including an elongated shaft that extends distally from the housing. The elongated shaft is configured to pass through a cannula or body orifice and defines a longitudinal axis therethrough. An end effector operably supported at the distal end of the elongated shaft includes a pair of jaw members. One of the jaw members is movable with respect to the other jaw member from an open position for positioning tissue therebetween, to a clamping position for grasping tissue therebetween. One or both of the jaw is/are activatable to one of electrosurgically and ultrasonically treat tissue. A selectively removable generator configured to pivotally couple to the housing is configured to convert electrical energy into at least one of RF and ultrasonic energy to energize the activatable jaw member. The generator defining one or more apertures at a distal end thereof and a pivot member disposed at a proximal end thereof. A locking mechanism configured to operably couple to the elongated shaft of the housing includes one or more locking fingers configured to releasably couple to the one or more apertures disposed at the distal end of the generator such that generator is selectively and removably engageable with the housing of the portable surgical instrument.

In certain instances, the one or more apertures may be further defined by three apertures.

In certain instances, the portable surgical instrument further includes a stationary guide finger that is configured to engage one of the three apertures on the generator and is configured to guide the remaining aperture(s) on the generator onto the locking finger(s) on the body portion to facilitate moving the locking finger(s) into the first position.

The locking finger(s) may be further defined by two or more locking fingers that are configured to releasably couple to two or more of the apertures. In this instance, the housing may include a pair of apertures defined therein that are configured to receive a respective one of the locking fingers. Moreover, and in this instance, the locking fingers are movable from a first position wherein the at least two locking fingers are configured to lock the generator to the housing, to a second position wherein the at least two locking fingers are configured to release the generator from the housing. The locking fingers each may include respective claw portions that are configured to facilitate engagement between the locking finger(s) and respective corresponding apertures on the generator.

The locking mechanism may include a body portion that is configured to pivotally support the locking fingers on sidewalls thereof.

The locking fingers each may include an engagement member disposed in a generally perpendicular orientation with respect to the respective claw portions. In this instance, the engagement members may be textured to facilitate movement of the locking fingers from the first position to the second position.

The locking finger(s) each may be pivotally supported on the sidewalls via respective arcuate medial portions.

The body portion of the locking mechanism may further define a channel that extends therethrough and is configured to receive the elongated shaft therein to facilitate supporting the locking mechanism to the shaft.

The locking mechanism may further includes an end cap that is configured to couple to a distal end of the housing.

The locking mechanism may be composed of two parts that are coupled to one another via a coupling method including without limitation press-fitting, snap-fitting and ultrasonic welding.

The portable surgical instrument may be a portable ultrasonic instrument and a portable electrosurgical instrument.

The portable surgical instrument may include a battery assembly that is configured to house a battery therein and configured to generate electrical energy that is utilized by the generator to generate one of the RF and ultrasonic energy.

Another aspect of the present disclosure provides a locking mechanism configured for use with a portable surgical instrument. The locking mechanism includes a body portion including an aperture defined therethrough. The body portion is adapted to couple to a housing of the portable surgical instrument. The body portion supports one or more movable locking fingers thereon. The one or more movable locking fingers is configured to releasably couple to one or more corresponding apertures disposed at the distal end of a generator that is adapted to selectively and removably engage the housing of the portable surgical instrument.

The locking finger(s) may be movable from a first position wherein the locking finger(s) is/are configured to lock the generator to the housing, to a second position wherein the locking finger(s) is/are configured to unlock the generator from the housing.

The locking finger(s) may include a claw portion that is configured to facilitate engagement between the locking finger(s) and the aperture(s) on the generator.

A stationary guide finger may be configured to engage an aperture on the generator and configured to guide the aperture on the generator onto the locking finger(s) on the body portion to facilitate moving the locking finger(s) into the first position.

BRIEF DESCRIPTION OF THE DRAWINGS

Various embodiments of the present disclosure are described hereinbelow with reference to the drawings, wherein.

DETAILED DESCRIPTION OF THE EMBODIMENTS

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

A locking mechanism 26, 126 (FIGS. 1A and 1B) in accordance with the present disclosure is configured for use with various handheld or portable surgical instruments (see FIGS. 1A and 1B) and is configured to selectively and removably couple a removable energy source, e.g., an electrosurgical and/or ultrasonic energy source, to the portable surgical instrument. For illustrative purposes, the locking mechanism 26, 126 is described in terms of use with an electrosurgical forceps 2 and an ultrasonic instrument 102, see FIGS. 1A and 1B, respectively.

Figure 1A:
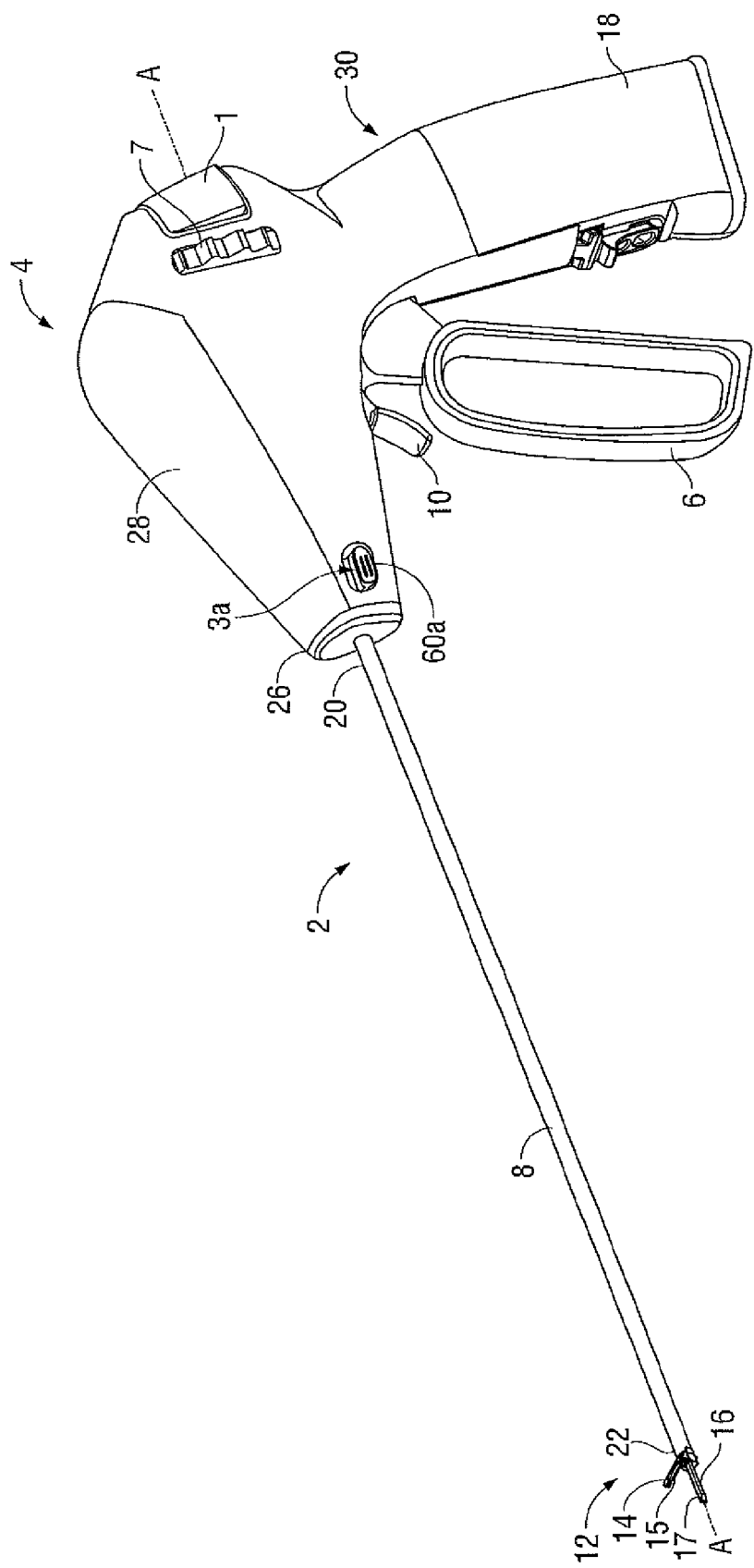
FIG. 1A is a side, perspective view of a battery-powered surgical instrument configured for use with a generator assembly according to an embodiment of the present disclosure.

With continued reference to FIG. 1A, a portable surgical instrument in the form of a bipolar electrosurgical forceps 2 (forceps 2) that is configured for use with locking mechanism 26 is illustrated. Forceps 2 is shown configured for use with various electrosurgical procedures and generally includes a housing 4, a battery assembly 18, a removable generator 28, a movable handle assembly 6, a rotating assembly 7, a trigger assembly 10, a drive assembly (not explicitly shown), and an end effector assembly 12 that operatively couples to the handle assembly 6 via the drive assembly for imparting movement of one or both of a pair of jaw members 14, 16 of end effector assembly 12.

Figure 6:
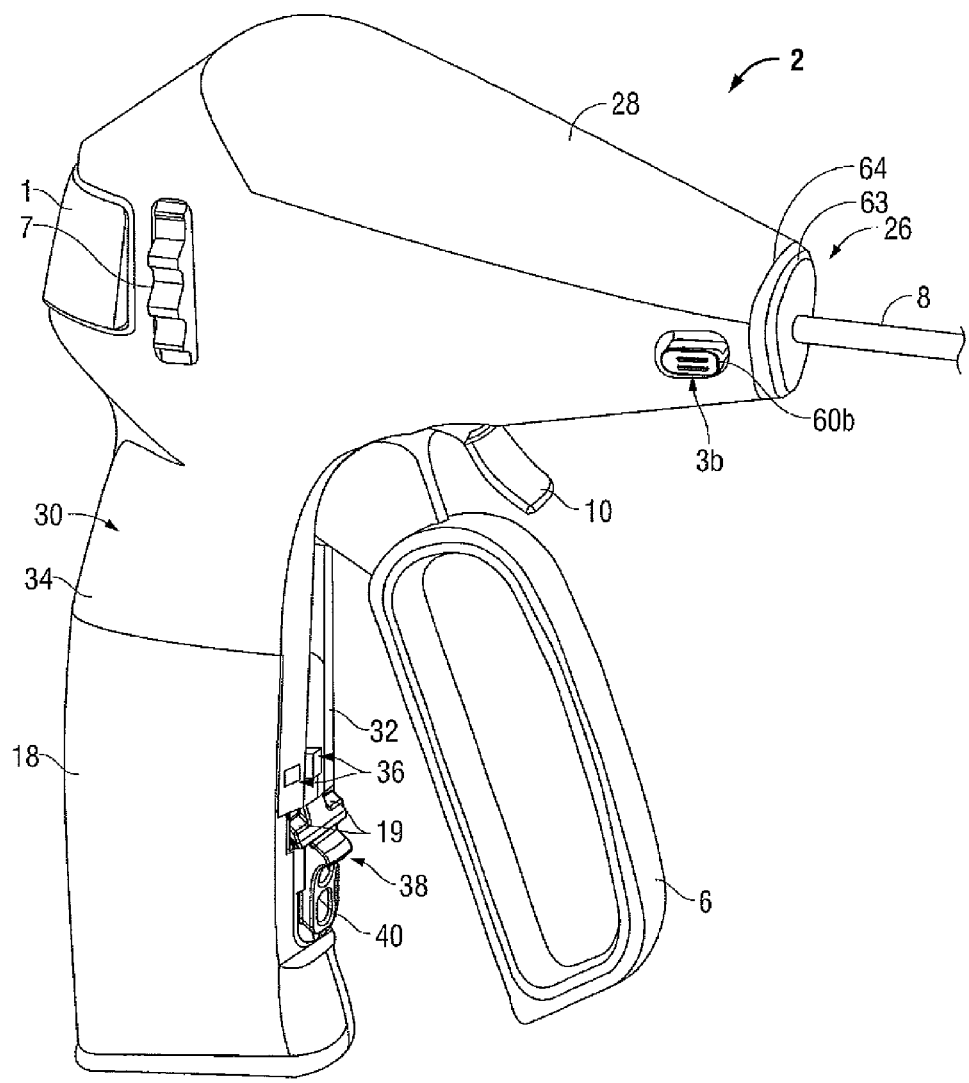
FIG. 6 is a partial, side perspective view of the battery-powered surgical instrument depicted in FIG. 1A with the generator attached.
Figure 7:
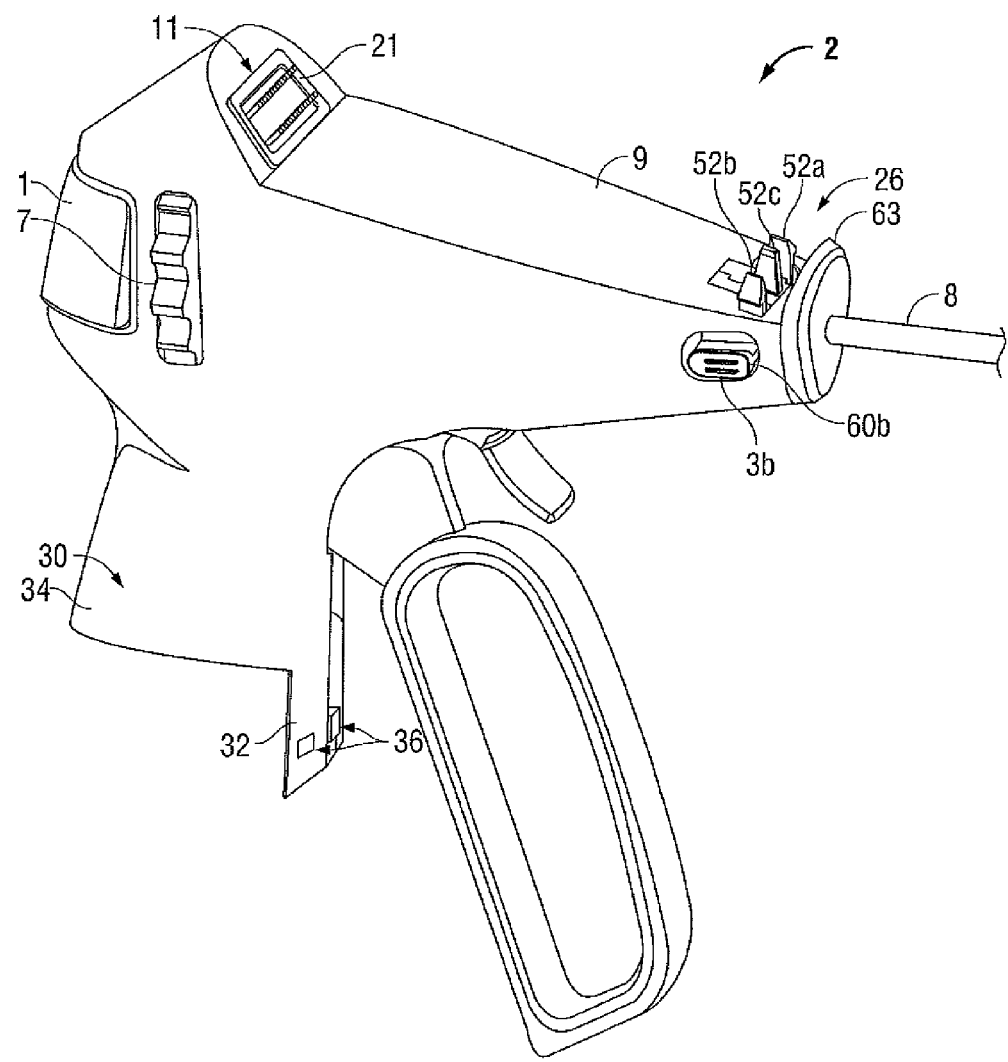
FIG. 7 is a partial, side perspective view of the battery-powered surgical instrument depicted in FIG. 6 with the generator and battery assembly unattached.

With reference to FIGS. 1A and 6-7, a proximal end of housing 4 is configured to releasably couple to an electrosurgical generator 28 (generator 28) and a battery assembly 18, described in greater detail below. A top surface 9 of the housing 4 is configured to releasably secure the generator 28 to the housing 4, see FIGS. 1A and 6-7. An aperture 11 (as best seen in FIG. 7) of suitable configuration is defined in a proximal end of the housing 4 and is configured to releasably engage a corresponding pivot member 13 (FIG. 2) on the generator 28. A multi-pin port connector 21 (FIG. 7) is disposed adjacent the aperture 11 and is configured to connect to a corresponding multi-slot array 23 (FIG. 2) on the generator 28. When connected to one another, the multi-pin port connector 21 and multi-slot array 23 provide an electrical interface that is configured to provide electrical communication between the forceps 2 and the generator 28. In particular, this electrical interface provides, inter alia, electrical continuity between the jaw members 14 and 16 and the generator 28 such that the jaw members 14 and 16 are capable of transmitting RF energy to tissue grasped therebetween.

With continued reference to FIGS. 1A and 6-7, distal end of the housing 6 is configured to support and/or couple to a proximal end 20 of a shaft 8. Shaft 8 extends from housing 6 and defines a longitudinal axis "A-A" therethrough (FIG. 1A). A pair of generally elongated apertures 3a and 3b of suitable configuration is defined in respective left and right sides at the distal end of housing 4, see FIGS. 1A and 6-7. The apertures 3A and 3b are configured to receive respective engagement members 60a and 60b therein, described in greater detail below.

The end effector 12 including jaw members 14 and 16 are supported at a distal end 22 of the shaft 8 (FIG. 1A). Jaw member 14 is pivotable about the jaw member 16 (and/or the distal end 22 of the shaft 18) and movable relative thereto when movable handle assembly 6 is moved proximally. More particularly, jaw member 14 is movable from an open position for positioning tissue between the jaw members 14 and 16, to a clamping position for grasping tissue between the jaw members 14 and 16. As noted above, the forceps 2 is of the bipolar type. That is, each of the jaw members 14 and 16 includes a respective seal plate 15 and 17 (FIG. 1A) that is configured to function as an active (or activatable) and/or return electrode. Each of the seal plates 15 and 17 is in operable communication with the generator 28 via one or more electrical leads that couple to the generator 28 and extend through the shaft 8 to the seal plates 15 and 17. In certain instances, it may prove advantageous to utilize a forceps 2 that is of a monopolar type. In this instance, one of the jaw members, e.g., jaw member 14 including seal plate 15, functions as an active electrode and a return pad (or other suitable device) may be utilized to function as the return electrode.

Battery assembly 18 is configured to releasably couple to the housing 4. To this end, housing 4 includes a docking portion 30 (FIGS. 1, 6 and 7) defined therein. Docking portion 30 includes an elongated member 32 (see FIG. 7) that extends in a generally perpendicular orientation with respect to a base member 34 and the longitudinal axis "A-A" (see FIGS. 1A and 7). The elongated member 32 includes one or more apertures 36 (see FIG. 7) that are configured to releasably engage one or more corresponding protrusions 19 disposed on the battery assembly 18. In the embodiment illustrated in FIG. 1A, the battery assembly 18 functions as a stationary handle and provides a gripping surface for a user.

A release latch 38 (FIG. 6) is operably disposed at a distal end of the battery assembly 18 and provides a mechanism to remove the battery assembly 18 from the forceps 2. More particularly, the release latch 38 is a "free-floating" part that is normally held in a retracted position by the elongated member 32. In order to uncouple the battery assembly 18 from the forceps 2, the release latch 38 is moved in a generally upward direction to a extended position that mechanically separates the battery assembly 18 from the forceps 2. Release latch 38 includes a bottom portion 40 (FIG. 6) that is ergonomically configured to receive a finger, e.g., a thumb, of a user.

Figure 2:
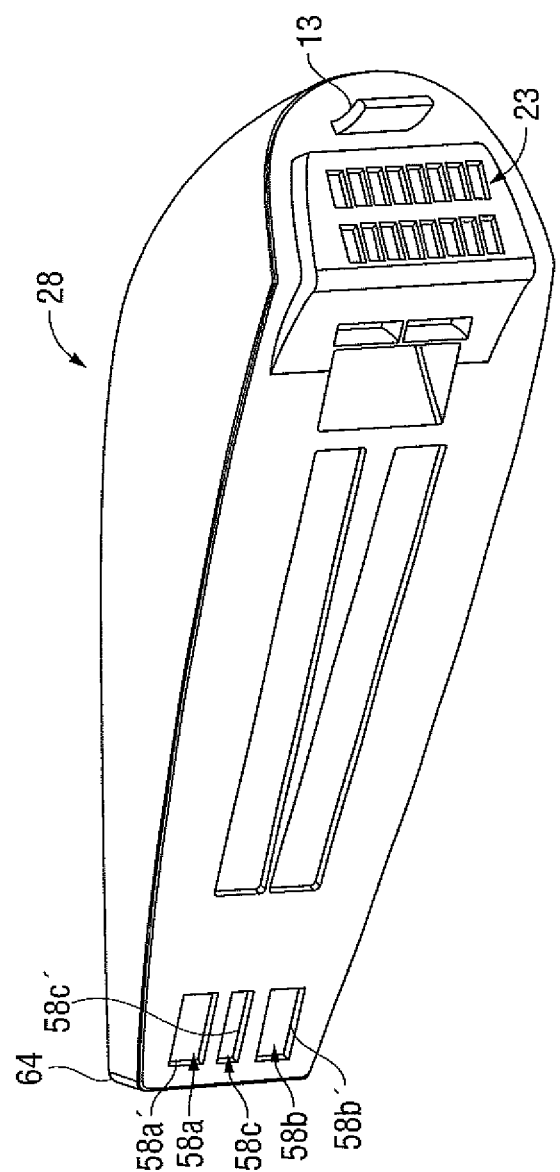
FIG. 2 is a perspective view illustrating a bottom of the generator depicted in FIG. 1A.

Generator 28 (FIGS. 1A, 2 and 6) operably couples to the housing 6 and may be selectively removable therefrom (FIG. 7) either in connection with removal of the battery assembly 18 or independently, as described in greater detail below. With this purpose in mind, a plurality of apertures 58a-58c (FIG. 2) are disposed at a distal end of the generator 28 and the pivoting member 13 (FIG. 2) is disposed at a proximal end of the generator 28. Apertures 58a-58b are configured to releasably couple to corresponding locking fingers 52a and 52b associated with the locking mechanism 26, described in greater detail below. Likewise, aperture 58c is configured to releasably engage a corresponding guide finger 52c associated with the locking mechanism 26 also described in greater detail below. Apertures 58a-58c are defined by respective peripheral walls 58a'-58c', as best seen in FIG. 2.

Generator 28 is in operable communication with the battery assembly 18 to provide electrosurgical energy at one or more suitable frequencies to the end effector 12 including the jaw members 14 and 16 to electrosurgically treat tissue, e.g., seal tissue. In particular, generator 28 includes electronics that converts the electrical energy from the battery assembly 18 into an RF energy waveform to energize one or both of the jaw members 14 and 16. That is, the generator 28 transmits the RF energy to the seal plates 15 and 17 to effect tissue treatment.

Trigger assembly 10 (FIG. 1A) is in operable communication with a knife or cutting assembly (not shown) including a cutting or knife blade that is configured to cut or sever tissue grasped between the jaw members 14 and 16 after tissue has been electrosurgically treated.

Rotating assembly 7 (FIG. 1A) is operable to rotate the shaft 8 including the end effector 12 about the longitudinal axis in either a clockwise or counter clockwise direction.

An activation button 1 (FIGS. 1A and 6-7) is disposed on housing 4 and is in operable communication with the generator 28. In particular, the activation button 1 is configured to selectively enable the generator 28 to generate and, subsequently, transmit RF energy to the seal plates 15 and 17 of the jaw members 14 and 16, respectively.

Figure 1B:
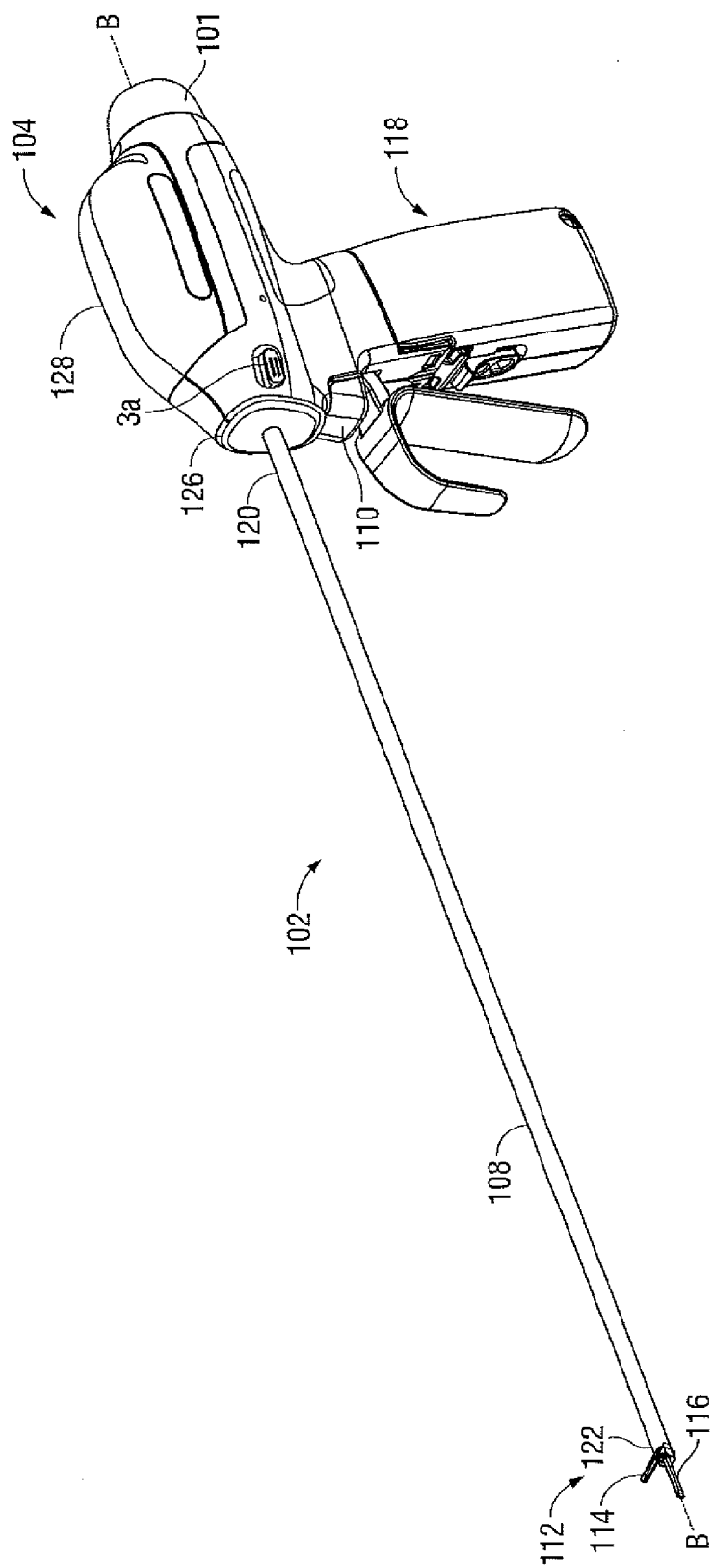
FIG. 1B is a side, perspective view of another type of battery-powered surgical instrument configured for use with a generator assembly according to an embodiment of the present disclosure.

With reference now to FIG. 1B, a battery-powered surgical instrument in the form of an ultrasonic instrument 102 that is configured for use with a locking mechanism 126 is illustrated. Instrument 102 includes components similar to that of forceps 2. Briefly, ultrasonic instrument 102 includes a housing 104 configured to house one or more components, e.g., transducer, waveguide and electrical circuitry that is configured for electrical communication with a battery assembly 118 of the instrument 102. A proximal end of housing 104 is configured to releasably couple to an ultrasonic generator 128 and the battery assembly 118. A distal end of the housing 104 is configured to support and/or couple to a proximal end 120 of a shaft 108. Shaft 108 extends from housing 104 and defines a longitudinal axis "B-B" therethrough (FIG. 1B). The operational parts of the end effector 112 (e.g., jaw members 114 and 116) are movable relative to one another upon actuation of a movable handle assembly 106 coupled to housing 104. End effector 112 includes jaw members 114 and 116 (FIG. 1B). In the embodiment illustrated in FIG. 1A, jaw member 116 serves as an active or oscillating blade and is configured to effect tissue. An activation button 110 places the instrument 102 in two modes of operation, a low-power mode of operation and a high-power mode of operation. Unlike generator 28, generator 128 is configured to convert the electrical energy produced by the battery assembly 118 into ultrasonic energy. More particularly, generator 128 includes a transducer (not explicitly shown) that is configured to convert electrical energy to mechanical energy that produces motion at an end of a waveguide (not explicitly shown) that is in operative communication with the active jaw member 116. When the transducer and waveguide are driven at their resonant frequency, they produce mechanical motion at the active jaw member 116.

Locking mechanisms 26, 126 are identical to one another and are configured for use with forceps 2 and instrument 102, respectively. Thus, for purposes of brevity, only the operable features of the locking mechanism 26 are described in detail.

With reference to FIGS. 1A and 3-7, locking mechanism 26 is illustrated. Locking mechanism 26 may be made from any suitable material including metal, ceramic, plastic, etc. In the illustrated embodiment, the locking mechanism 26 is formed from a relatively rigid plastic. Locking mechanism 26 is formed by coupling or joining two substantially identical injection molded locking mechanism half portions 26a and 26b (half portions 26a and 26b) to one another. In the illustrated embodiment, the half portions 26a and 26b are joined to one another via a press-fit, friction fit, ultrasonic welding or the like. In the illustrated embodiment, one of the half portions, half portion 26a, includes one or more indents 48 (FIG. 5) and the other half portion, e.g., half portion 26b, includes one or more corresponding detents (not explicitly shown) that are configured to securely engage the corresponding intents, see FIG. 3 in combination with FIG. 5. Alternatively, the locking mechanism 26 may be of unitary construction.

Figure 3:
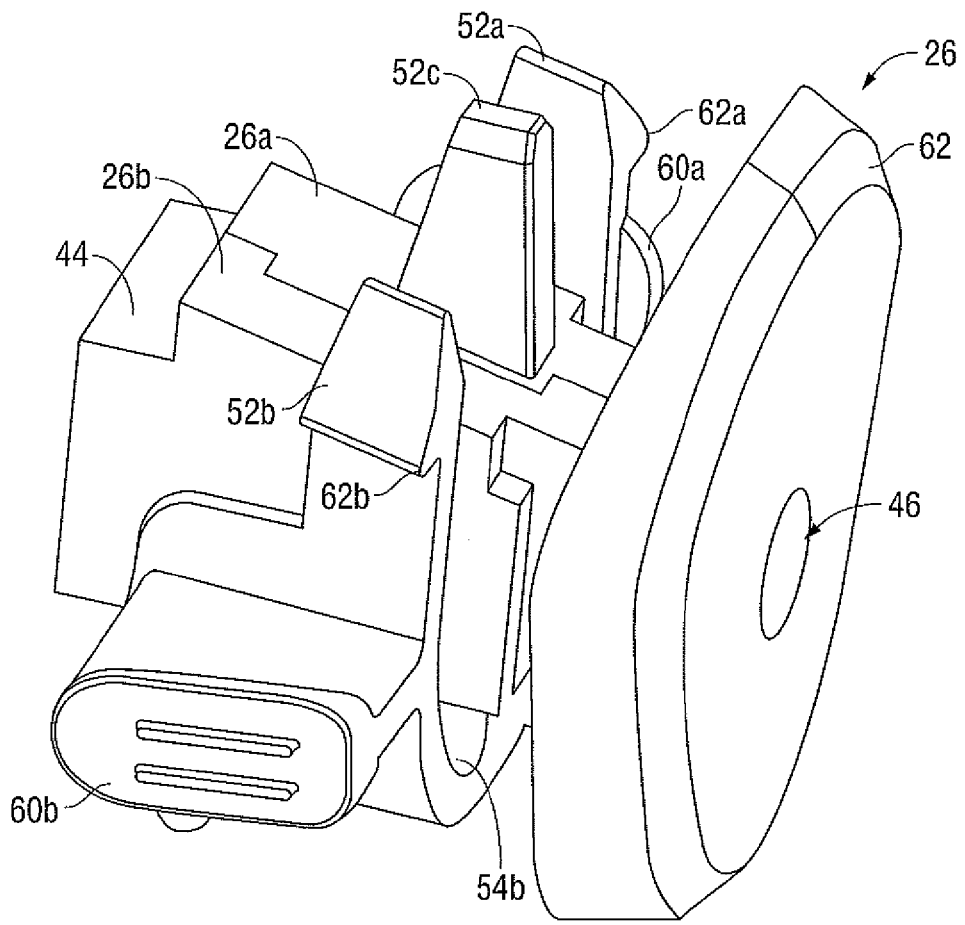
FIG. 3 is an enlarged, perspective view of a locking mechanism utilized to selectively and removably couple the generator to the battery-powered surgical instrument depicted in either of FIG. 1A or 1B.
Figure 4:
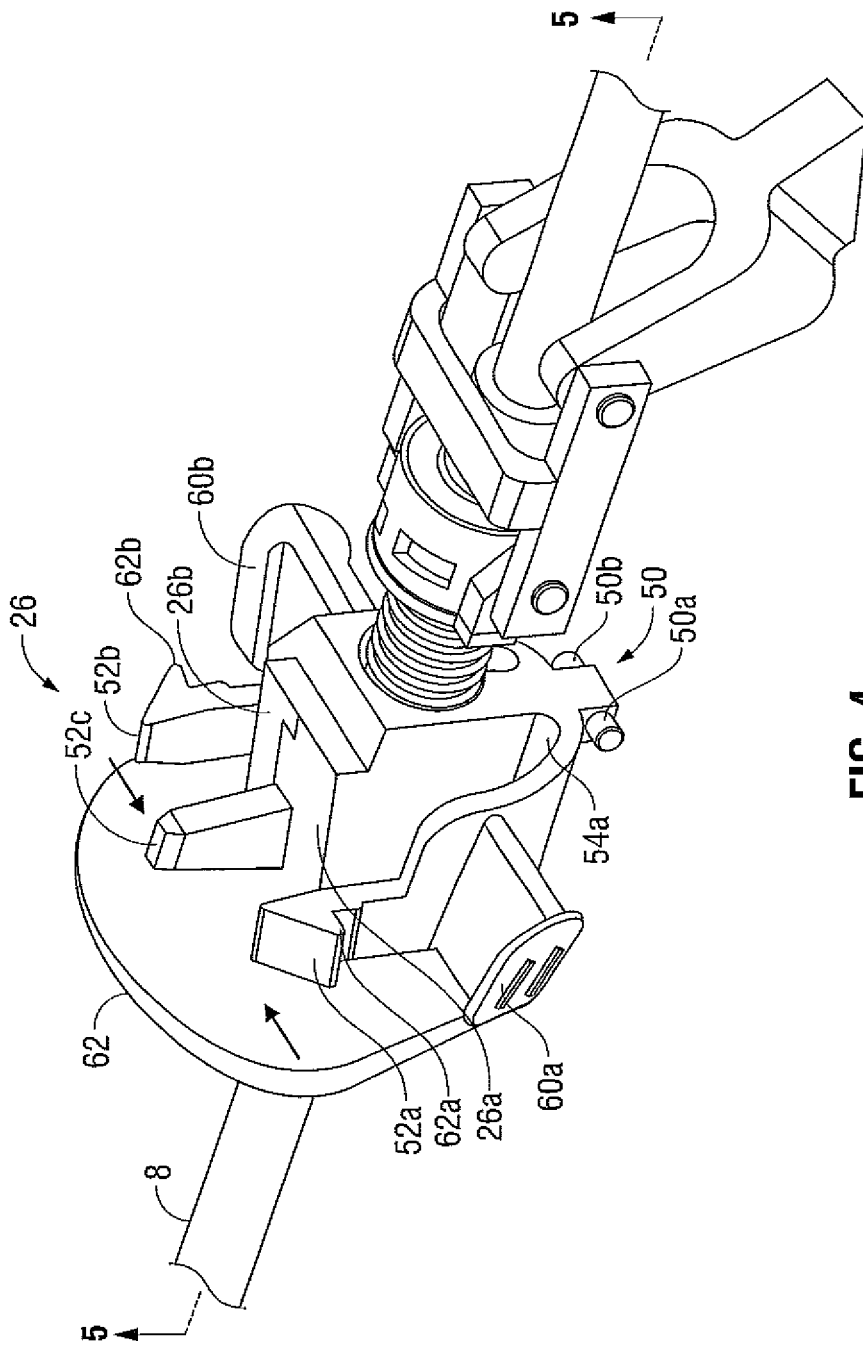
FIG. 4 is a rear, perspective view of the locking mechanism depicted in FIG. 3 attached to a shaft of the battery-powered surgical instrument depicted in FIG. 1A with a housing thereof removed.
Figure 5:
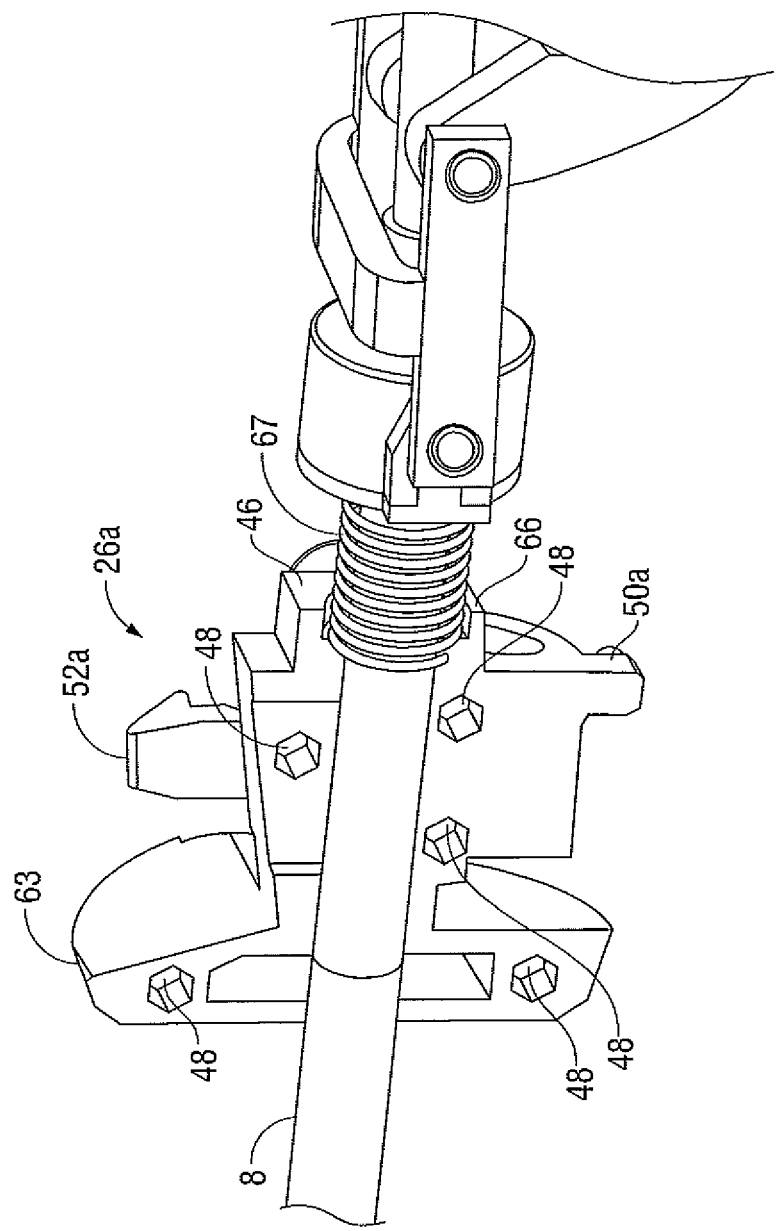
FIG. 5 is a partial, cut-away view taken along the line-segment "5-5" of FIG. 4.

Continuing with reference to FIGS. 1A and 3-7, locking mechanism 26 is configured to selectively and removably couple the generator 28 to the housing 4. To this end, locking mechanism 26 operably couples to the elongated shaft 8 of the housing 4 by one or more suitable coupling methods. More particularly, the locking mechanism 26 includes a body portion 44 that is defined by the half portions 26a and 26b when the half portions 26a and 26b are in the assembled configuration, see FIGS. 3 and 4. A channel or passageway 46 is defined through the body portion 44 and is configured to receive the shaft 8 therein to facilitate supporting the locking mechanism 26 to the shaft 8 (FIGS. 4 and 5). A bottom leg or support post 50 (FIG. 4) is disposed at a bottom end of the body 44 and is configured to couple to an internal frame of the housing 4. Bottom leg 50 is defined by bottom leg half portions 50a and 50b of half portions 26a and 26b, respectively, as best seen in FIG. 4.

Locking fingers 52a and 52b (FIGS. 3 and 4), are pivotally supported on the body portion 44 and are configured to selectively and releasably couple to corresponding apertures 58a and 58b (FIG. 2) disposed at the distal end of the generator 28. In particular, in the assembled configuration, each half portion 26a and 26b functions as respective left and right sidewalls for the body portion 44 and supports the locking fingers 52a and 52b thereon. Locking fingers 52a and 52b include respective generally arcuate medial portions 54a (FIG. 4) and 54b (FIG. 3) that allow the locking fingers 52a and 52b to pivot about the body portion 44 when the engagement members 60a and 60b are pressed by a user. It should be noted that the arcuate medial portions 54a and 54b may function similar to that of what is typically referred to in the art as a "living hinge." Locking fingers 52a and 52b are movable or pivotable about the arcuate medial portions 54a and 54b from a first position wherein the locking fingers 52a and 52b are configured to lock the generator 28 to the housing 4, to a second position wherein the locking fingers 52a and 52b are configured to unlock the generator 28 from the housing 4.

To facilitate pressing the locking fingers 52a and 52b such that the locking fingers 52a and 52b pivot about the body portion 44, each locking finger 52a and 52b includes a respective engagement member, see FIGS. 3 and 4. Each engagement member 60a and 60b is textured to facilitate a user in moving the locking fingers 52a and 52b from the first position to the second position. The engagement members 60a and 60b are disposed in a generally perpendicular orientation with respect to respective claw portions 62a and 62b disposed on the locking fingers 52a and 52b (FIGS. 3 and 4).

Respective claw portions 62a and 62b are configured to facilitate engagement between the locking fingers 52a and 52b and the respective apertures 58a and 58b on the generator 28. In the illustrated embodiment, the claw portions 62a and 62b include a generally "hook" shape that facilitates maintaining the locking fingers 52a and 52b in an engaged configuration (e.g., in the first position) when the locking fingers 52a and 52b are positioned within the apertures 58a and 58b. The claws 62a and 62b are in vertical registration with the respective peripheral walls 58a' and 58b' such that a portion thereof is configured to contact the claws 62a and 62b as locking fingers 52a and 52b are being positioned into the respective apertures 58a and 58b.

An end cap 62 (FIGS. 1A and 3-7) is formed at a distal end of the body portion 44. The end cap 62 is configured to facilitate in maintaining the generator 28 in a relatively fixed orientation when the generator 28 is coupled to the housing 4. End cap 62 includes a generally flat configuration and engages a flat wall of the housing. In embodiments, however, end cap 62 may include a lip or flange 63 extends along an outer peripheral edge of the end cap 62. In this instance, flange 63 is configured to grasp or latch onto a corresponding ridge 64 (FIG. 2) located at the distal end of the generator 28, as best seen in FIG. 6.

An optional guide finger 52c is configured to engage the aperture 58c on the generator 28 and is configured to guide the apertures 58a and 58b on the generator 28 onto the corresponding locking fingers 52a and 52b on the body portion 44 to facilitate moving the locking fingers 52a and 52b into the first position. Guide finger 52c is configured to align the generator 28 and locking fingers 52a and 52b to ensure equal engagement between both locking fingers 52a and 52b and apertures 58a and 58b; thus, the generator 28 will remain securely coupled to the housing 6, even in instances where the generator 28 is side loaded. Moreover, the guide finger 52c ensures that both locking fingers 52a and 52b engage the respective apertures 58a and 58b at the same time, giving a more secure-feeling "tactile click" when the generator 28 is attached to the housing 6. Further, a distal surface of the guide finger 52c acts as a cam to force the generator 28 proximally as it is rotated into position and clipped into place.

In the illustrated embodiment, a proximal end of the body portion 44 forms a cavity 66 that is configured to receive a portion of a spring 67. The spring 67 functions in cooperation with the drive assembly to return a blade mechanism (not explicitly shown) to its retracted position.

In use, battery assembly 18 is, initially, in a prepackaged condition or secured to a battery charger docking station (not shown) and unattached to the housing 4 (FIG. 7). Similarly, the generator 28 is, initially, in a prepackaged condition or secured to a generator charger docking station (not shown) and unattached to the housing 4 (FIG. 7). To attach the generator 28 to the housing 4, a user positions the pivoting member 13 on the generator 28 into the aperture 11 located on the top surface of the housing 4. Thereafter, the user pushes the distal end of the generator 28 downward and toward the locking fingers 52a and 52b and the guide finger 52c. The guide finger 52c engages the aperture 58c to guide the apertures 58a and 58b onto the locking fingers 52a and 52b. As the locking fingers 52a and 52b are being positioned into the apertures 58a and 58b, claw portions 62a and 62b contact the respective peripheral walls 58a' and 58b', which, in turn, bends or flexes the locking fingers 52a and 52b outwardly about the concave medial portions 54a and 54b to the second position. The locking fingers 52a and 52b continue to flex until the claws 62a and 62b engage an interior surface of the generator 28 at which time the locking fingers 52a and 52b return to the first position. The lip 63 on the end cap 62 engages the ridge 64 to facilitate in maintain the generator 28 in a relatively fixed orientation about the housing 4.

To remove the generator 28, a user pushes the engagement members 60a and 60b, which, in turn disengages the claws 64a and 64b from the interior surface of the generator 28, while moving the generator 28 in a relatively upward direction.

The unique locking mechanism 26 of the present disclosure enables a user to quickly and easily couple and uncouple the generator 28 from the housing 4 of the forceps 2 without the need of any additional devices and/or mechanisms.

As can be appreciated, use of the locking mechanism 126 is substantially similar to that of the locking mechanism 26 and, as a result thereof, will not be described in detail.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A portable surgical instrument, comprising:
  a housing including an elongated shaft extending distally therefrom, the elongated shaft defining a longitudinal axis therethrough, the housing including an aperture defined therein;
  an end effector operably supported at the distal end of the elongated shaft, the end effector including a pair of jaw members, at least one of the jaw members movable with respect to the other jaw member from an open position for positioning tissue therebetween, to a clamping position for grasping tissue therebetween, at least one of the jaw members activatable to treat tissue;

a selectively removable generator configured to pivotally couple to the aperture of the housing to energize the at least one activatable jaw member, the generator defining at least one aperture at a distal end thereof and a pivot member disposed at a proximal end thereof; and a locking mechanism operably coupled to the elongated shaft of the housing, the locking mechanism including at least one locking finger configured to releasably couple to the at least one aperture disposed at the distal end of the generator such that the generator is selectively and removably engageable with the housing of the portable surgical instrument.

2. A portable surgical instrument according to claim 1, wherein the at least one aperture of the generator is further defined by at least three apertures.

3. A portable surgical instrument according to claim 2, further including a stationary guide finger configured to engage at least one of the at least three apertures on the generator and configured to guide the at least one aperture on the generator onto the at least one locking finger of the locking mechanism to facilitate moving the at least one locking finger into the first position.

4. A portable surgical instrument according to claim 2, wherein the at least one locking finger is further defined by at least two locking fingers that are configured to releasably couple to at least two of the at least three apertures.

5. A portable surgical instrument according to claim 4, wherein the housing includes a pair of apertures defined therein configured to receive a respective one of the at least two locking fingers.

6. A portable surgical instrument according to claim 5, wherein the locking mechanism includes a body portion configured to pivotally support the at least two locking fingers on sidewalls thereof.

7. A portable surgical instrument according to claim 6, wherein the at least two locking fingers are each pivotally supported on the sidewalls via respective arcuate medial portions.

8. A portable surgical instrument according to claim 6, wherein the body portion of the locking mechanism further defines a channel extending therethrough, the channel configured to receive the elongated shaft therein to facilitate supporting the locking mechanism to the shaft.

9. A portable surgical instrument according to claim 4, wherein the at least two locking fingers are movable from a first position wherein the at least two locking fingers are configured to lock the generator to the housing, to a second position wherein the at least two locking fingers are configured to release the generator from the housing.

10. A portable surgical instrument according to claim 9, wherein the at least two locking fingers each includes respective claw portions that are configured to facilitate engagement between the at least two locking fingers and respective corresponding apertures on the generator.

11. A portable surgical instrument according to claim 10, wherein the at least two locking fingers each include an engagement member disposed in a generally perpendicular orientation with respect to the respective claw portions.

12. A portable surgical instrument according to claim 11, wherein each of the engagement members is textured to facilitate movement of the at least two locking fingers from the first position to the second position.

13. A portable surgical instrument according to claim 1, wherein the locking mechanism further includes an end cap that is configured to couple to a distal end of the housing.

14. A portable surgical instrument according to claim 1, wherein the locking mechanism is composed of two parts.

15. A portable surgical instrument according to claim 1, wherein the portable surgical instrument is one of a portable ultrasonic instrument and a portable electrosurgical instrument.

16. A portable surgical instrument according to claim 15, further including a battery assembly configured to house a battery therein and configured to generate electrical energy that is utilized by the generator to generate one of RF and ultrasonic energy.

* * * * *